United States Patent
von Fuchs

(10) Patent No.: US 6,763,837 B2
(45) Date of Patent: Jul. 20, 2004

(54) ARRANGEMENT FOR MOUNTING A COUNTER-PRESSURE PLATE FOR A SHAFT-LIKE SURGICAL SUTURING DEVICE

(76) Inventor: Alexander von Fuchs, Garsberg 1, 5020 Salzburg (AT)

( * ) Notice: Subject to any disclaimer, the term of this patent is extended or adjusted under 35 U.S.C. 154(b) by 16 days.

(21) Appl. No.: 10/183,433

(22) Filed: Jun. 22, 2002

(65) Prior Publication Data

US 2002/0188320 A1 Dec. 12, 2002

Related U.S. Application Data

(63) Continuation-in-part of application No. PCT/EP00/13172, filed on Dec. 22, 2000.

(51) Int. Cl.[7] .............................................. A61B 17/28
(52) U.S. Cl. ..................... 128/898; 227/175.1; 604/909
(58) Field of Search .......................... 227/179.1, 180.1; 604/909

(56) References Cited

U.S. PATENT DOCUMENTS

| | | | | |
|---|---|---|---|---|
| 3,926,195 A | * | 12/1975 | Bleier et al. ................ 128/831 |
| 4,351,466 A | * | 9/1982 | Noiles ............................ 227/8 |
| 4,665,917 A | * | 5/1987 | Clanton et al. ............. 606/153 |
| 4,803,985 A | * | 2/1989 | Hill .............................. 606/157 |
| 4,844,068 A | * | 7/1989 | Arata et al. ............... 227/175.1 |
| 4,999,747 A | * | 3/1991 | Chen .......................... 362/103 |
| 5,074,868 A | * | 12/1991 | Kuzmak ..................... 606/157 |
| 5,449,368 A | * | 9/1995 | Kuzmak ..................... 606/157 |

FOREIGN PATENT DOCUMENTS

| | | | | |
|---|---|---|---|---|
| DE | 3300768 C | * | 4/1985 | ........... A61B/17/11 |
| DE | 3301713 C | * | 11/1989 | ........... A61B/17/11 |

* cited by examiner

Primary Examiner—Gary Jackson
(74) Attorney, Agent, or Firm—Klaus J. Bach

(57) ABSTRACT

In arrangement for supporting a counter pressure plate of a shaft-like surgical clamp suturing instrument for establishing a circular seam, a shaft-like clamp suturing instrument having at its distal end a support and guide structure and a one-piece support structure axially movably supported on the support and guide structure and having a support portion extending normal to the shaft section and releasable engaging a back-pressure plate in a position where the back-pressure plate is in axial alignment with the shaft section.

12 Claims, 10 Drawing Sheets

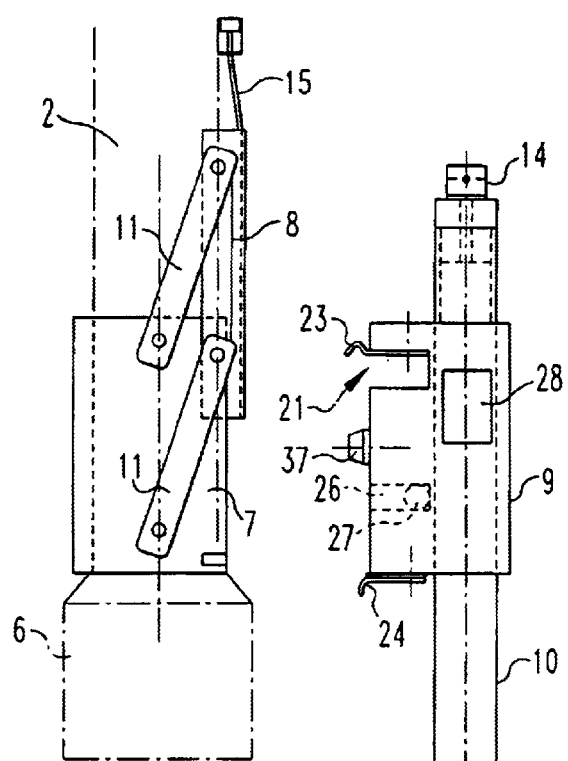
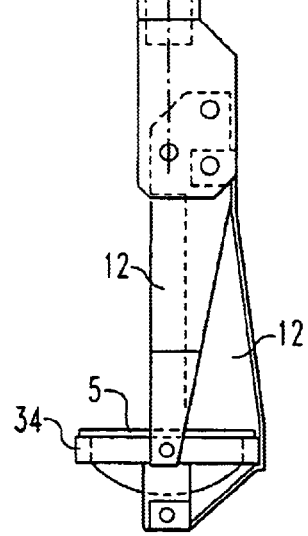
FIG.2

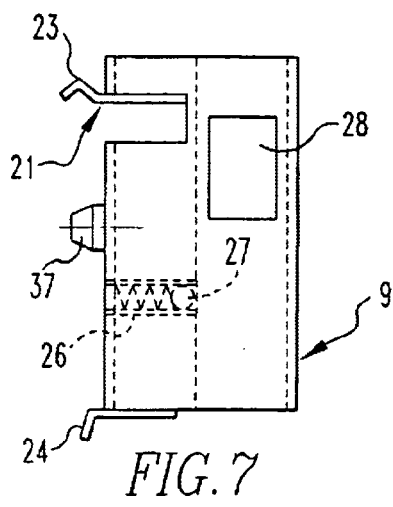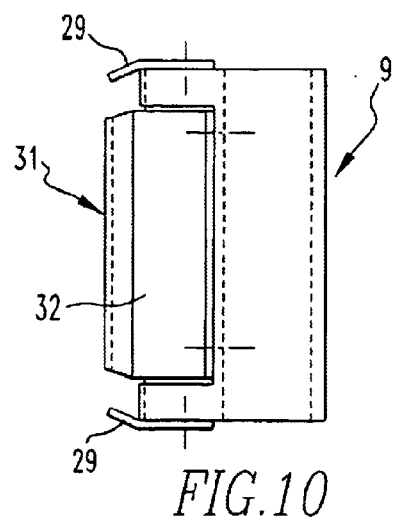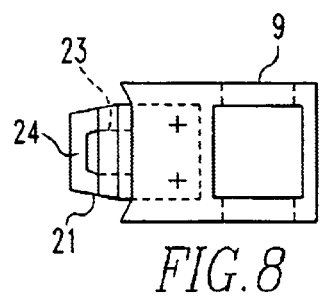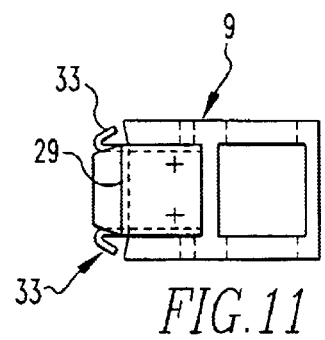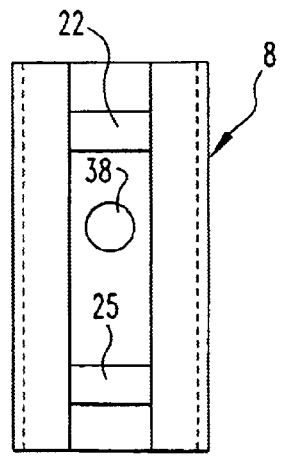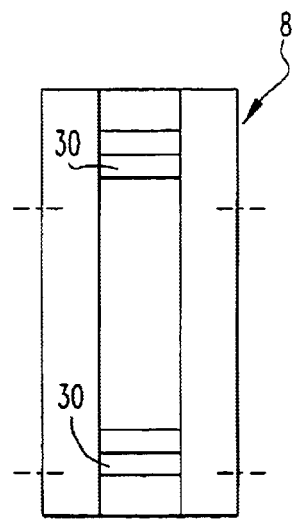

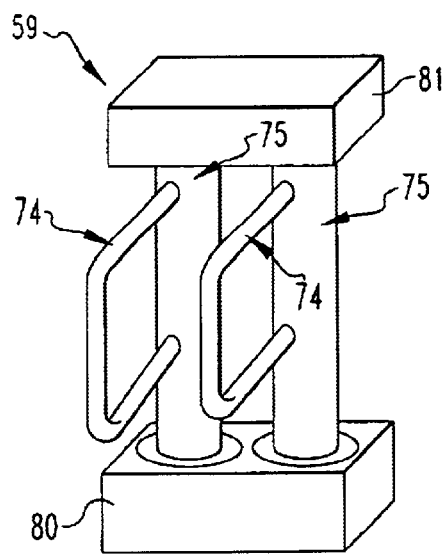
FIG.18
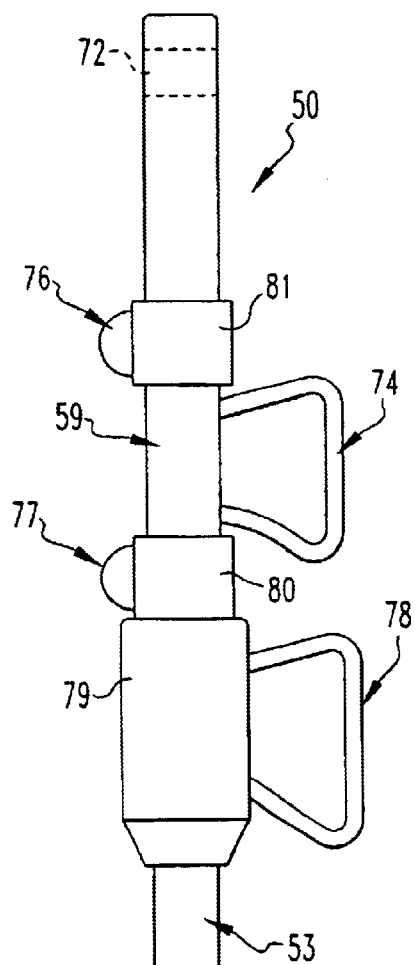
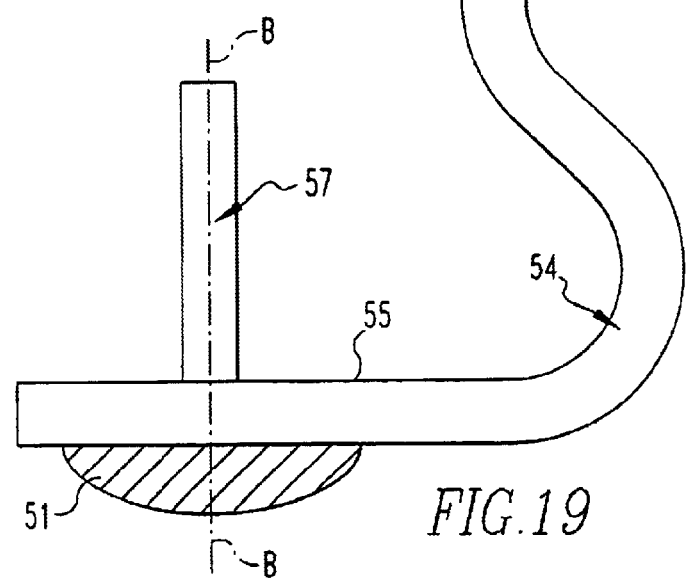
FIG.19

US 6,763,837 B2

ARRANGEMENT FOR MOUNTING A COUNTER-PRESSURE PLATE FOR A SHAFT-LIKE SURGICAL SUTURING DEVICE

This is a continuation-in-part application of international application PCT/EP00/13172 filed Dec. 22, 2000 and claiming the priority of German application 199 62 581.6 filed Dec. 23, 1999.

BACKGROUND OF THE INVENTION

The invention relates to an arrangement for a functional support of a counter-pressure plate for a shaft-like surgical stapling instrument, particularly a laparoscope VBG (Vertical Band Gastroplastic) according to Mason, wherein a hole has to be punched into the front and the rear stomach walls which is done using a circular stapler.

With such laparoscopic surgeries, a stapler provided with a thorn is pushed from the front toward the back or vice-versa through the front and rear stomach walls and then connected to a counter pressure plate. By way of this hole, the stomach fundus is separated and the exit is surrounded by a band so that it cannot expand. Because of large difficulties to join the counter pressure plate behind the stomach to the thorn of the stapler and the danger of injuring directly adjacent organs such as the pancreas or large vessels, this surgery is generally performed in an open surgical procedure. So far, it is performed laparoscopically only in a few centers worldwide.

With the surgical stapling instruments known so far from DE OS 3 300 768 and DE PS 3 301 713 for the interconnection of two organ walls, the connection between the thorn and the counter pressure plate depends essentially on the experience and the sense of touch of the surgeon and is possible reliably only by open surgery.

It is the object of the invention to provide for the laparoscopically experienced surgeon an appartus for a functionally correct support of a counter pressure plate for a rod-like surgical clamp suturing instrument like an aiming device which facilitates a simple and safe connection by the clamp suturing instrument or, respectively, the circular stapler and the counter pressure plate.

SUMMARY OF THE INVENTION

In arrangement for supporting a counter pressure plate of a shaft-like surgical clamp suturing instrument for establishing a circular seam, a shaft-like clamp suturing instrument having at its distal end a support and guide structure and a one-piece support structure axially movably supported on the support and guide structure and having a support portion extending normal to the shaft section and releasable engaging a back-pressure plate in a position where the back-pressure plate is in axial alignment with the shaft section.

With the arrangement according to the invention, the laparoscopically experienced surgeon receives a safe auxiliary device for a reliable interconnection of a stapler and a counter pressure plate behind the stomach. At the same time, the arrangement according to the invention provides for a design and construction, which prevents injuries to surrounding organs and vessels.

The device can be easily attached to shaft sections of circular staplers or clamp suturing instruments and preferably consists only of single-part support member which, because of its shape, can be easily inserted behind the stomach wall and can also be properly adjusted for an accurate alignment of the counter-pressure plate for the intended connection because of its adjustable mounting on the shaft section and the removable support member for the counter pressure plate.

In a preferred embodiment of the invention the support member has a clasp-like shape wherein the engagement section for the counter pressure plate is provided at a widened end. The clasp-like shape combines the advantages of a rounded profile structure, which provides for small chances of injuries and those of simple manufacturing.

Preferably, the support section for the counter pressure plate comprises two semi-circular sections including an at least partially form fitting reception area for the outer contour of the counter pressure plate. These measures provide for safe positioning of the counter pressure plate for the intended connection with the thorn, which is extendable from the stapler. Preferably, the semicircular sections can be spread apart against the force of a spring structure which force preferably also provides for engagement of the counter pressure plate in the support section in order to ensure, together with the form fitting engagement, the safe retaining of the counter pressure plate.

In a preferred embodiment of the invention, the support member includes a sled-like mounting section which can be attached to a complementary profile section of a support and guide structure mounted on a distal end of the clamp suturing instrument such that it is movable between at least two engagement positions and is removable from the support and guide structure. Such an arrangement permits the support structure to be moved behind the stomach while in a first engagement position in which it is located further removed from the distal end of the clamp suturing instrument. After reaching the predetermined operating position, the support structure can be moved closer to the distal end of the thorn of the stapler to which it is to be coupled. After the pressure plate and the thorn have been joined, the stomach walls have been moved together and the holes have been punched, the support member can be removed in a simple manner from the counter pressure plate by backsliding of the support structure. Then the support member can be removed from the support and guide structure and deposited for removal from the operation area.

The movable mounting section of the support member preferably includes two parallel clamping legs and horizontal transverse sections. Preferably, the movable section of the mounting member is provided with at least tow disengageable locking members for securing the rest positions formed on the support and guide structure. The locking members are preferably self-engaging members such as spring-loaded balls which are received in corresponding recesses formed on the support and guide structure.

For the attachment of the support and guide structure, preferably a two-part mounting sleeve, which can easily be mounted, is provided. It includes a shot mounting section and a profiled section for the mounting section. The two mounting sleeve parts include sections, which are in engagement with each other.

For the release and the movement of the mounting part, at least one yoke-like handling structure is provided.

To facilitate the removal of the support member, in accordance with another embodiment of the invention, the support member is provided, at its end opposite the engagement section, with a structure for the attachment of a pull member.

In accordance with still another embodiment of the invention, a surgical clamping device for forming circular sutures is provided. It comprises a one-piece support member with a sidewardly projecting portion, which forms at its end an engagement portion for the releasable engagement of the counter pressure plate. A guide structure, which is removably mounted on the device shaft, is provided for the positioning of the counter pressure plate. Particularly the coupling of the counter pressure plate and the clamp suturing instrument by means of a guide structure ensures that the counter-pressure plate is moved toward the pull member or, respectively, the clamp magazine in its proper position and that a proper adaptation of the counter pressure plate is provided with the pull member. The releasable connection of the guide structure to the device shaft facilitates the separate introduction of the guide structure and the device shaft of the clamp-suturing instrument by way of a trocar. The guide structure and the device shaft are than interconnected within the belly of the patient. The separation of the equipment shaft and the guide structure is necessary since the diameter of the trocar is generally only slightly greater than the diameter of the clamp magazine so that the insertion of the device shaft with the guide structure attached thereto is impossible for most applications.

In a preferred embodiment, the guide structure according to the invention comprises a guide means which may be coupled to the device shaft by a coupling, a guide tube which is axially movably supported in the guide means and a support structure arranged at one end of the guide tube for receiving the counter pressure plate. The coupling for the interconnection of the guide structure with the device shaft comprises a mounting portion which surrounds the device shaft and which is preferably a clamping sleeve, and a coupling plate for the connection of the guide means to the mounting portion. To facilitate the insertion of the device shaft into the belly of the patient through the trocar the mounting part and the coupling plate of the coupling may be pivotally interconnected by means of two parallelogram-like lever pairs such that the coupling plate can be pivoted toward the device shaft whereby the circumference of the clamp suturing instrument is reduced. To this end, preferably the surface contour of the coupling plate facing the device shaft is adapted to the surface contour of the device shaft such that the coupling plate abuts the device shaft in a form-fitting manner in the collapsed insert position.

The lever pairs of the coupling can be pivoted by means of a linkage or a tackle, which is connected directly to the coupling plate and which includes a handle and is supported on the device shaft or respectively, the operating handle of the clamp suturing instrument. If a tackle is used, it is advantageous if furthermore at least one return spring is provided for the return of the coupling plate from the insertion position in which the coupling plate is pivoted onto the device shaft to the extended operating position. The return spring is connected with one end either to the coupling plate or at least one lever pair. The other end is mounted to a mounting structure.

In another preferred embodiment, the coupling is returned to an operating position by means of two parallel return springs which are connected with one end to the connecting plate and with the opposite end to the mounting structure.

In a further embodiment, half of the coupling is connected to the device shaft and the support for the counter pressure plate is connected to the guide tube by way of lever pairs such that the pivoting of the lever pair results in an orientation of the counter pressure plate which is co-axial with the device plate.

In connection herewith, the lever pair assigned to the coupling may be two parallelogram levers which, in the axial direction of the device are disposed on top of one another and between the device shaft and the associated coupling half of the coupling, whereas the lever pair assigned to the support structure for the counter pressure plate is arranged at the end of the guide tube wherein the connecting arm axes at the guide tube are disposed on top of one another in the longitudinal direction of the guide tube.

To facilitate the insertion of the guide structure into the trocar, the counter pressure plate can be pivoted together with the support structure thereof by means of a lever pair connected to the support structure from an operating position in which it extends parallel to the axis of the guide tube to an insert position in which it is disposed co-axially with the guide tube, wherein a coupling pin arranged concentrically on the counter pressure plate is disposed between the lever pair.

In order to permit actuation of the lever pair assigned to the support of the counter pressure plate when the guide structure is inserted in the trocar, an operating linkage is disposed in the guide tube, which, with one end, is connected to one of parallelogram levers of the support for the counter pressure plate and, with the other end, to a hand operating structure for the manual operation.

To avoid an unintended movement of the support structure for the counter pressure plate out of the operating position spring means are provided on the guide and the adjustment linkage, which bias the adjustment linkage in a position corresponding to the operating position of the counter-pressure plate so that the counter-pressure plate can be removed out of the operating position only against this spring force.

In order to ensure proper operation of the guide structure, a connection with accurate relative positions of the guide structure and the coupling plate are required. In order to ensure that the parts to be joined are accurately positioned the guide structure includes a centering pin which cooperates with a correspondingly-shaped centering bore in the connecting plate.

The guide structure is then fixed to the coupling plate by means of spring clamps or by resilient engagement tongues disposed on the guide structure, which are received in corresponding engagement recesses of the coupling plate.

In order to ensure a safe connection of the coupling part of the guide structure, the front side of the guide structure is provided with an angled support member which projects beyond the contour of the guide structure. The support member is received in a correspondingly shaped recess of the coupling plate and accommodates the forces resulting from the engagement tongue or engagement spring mounting arrangement.

Alternately, a guide panel which extends beyond the outer contour of the guide structure may be arranged at two opposite surfaces of the guide sleeve which guide panels cooperates with a complementary guide surface at the connecting plate. The spring tongues or spring clamps are so arranged at the guide structure that the effective directions of the guide panels and the retaining springs are displaced by 90°. In connection with this spatial arrangement of retaining clamps and guide panels, it has also been found to be advantageous to utilize a U-shaped spring clamp and about V-shaped bent-over end sections at the ends of the spring arms.

In order to provide for a secure axial locking of the guide tube within the guide structure, the guide structure includes a spring-loaded engagement means, which is spring biased in radial direction and which cooperates with corresponding engagement recesses or marks on the shaft of the support structure. Preferably, the engagement means consists of an engagement ball, which is disposed in a radial bore in the guide and is engaged by a compression spring.

The guide tube is prevented from rotation by providing the guide tube with a shape other circular and the guide structure surrounds the guide tube in a form-fitting relationship. Preferably, the guide tube has an oval cross-section.

The support structure for the counter pressure plate is essentially annular and includes two radial clamping jaws which are connected by two shaft sections to the lever pairs so as to be pivotable about an axis which extends parallel to the pivot axis of the lever pairs.

Below, the invention will be described in greater detail in the reference to the accompanying drawings.

BRIEF DESCRIPTION OF THE DRAWINGS

FIG. 2 is a side view of the guide structure of the shaft in insertion position, FIG. 7 is a side view of the guide structure, FIG. 8 is a top view of the guide structure as shown in FIG. 7, FIG. 9 is a side view of a coupling plate for connection to the guide structure shown in FIG. 7, FIG. 10 is a side view of another embodiment of the guide structure, FIG. 11 is a top view of the guide structure according to FIG. 10, FIG. 12 is a side view of a coupling plate for the connection of the guide structure of FIG. 10, FIG. 18 is a partial perspective view of the mounting structure for the support structure and FIG. 19 is a schematic side view of the support structure in the counter pressure plate supported thereon.

DESCRIPTION OF PREFERRED EMBODIMENTS

Figure 1:
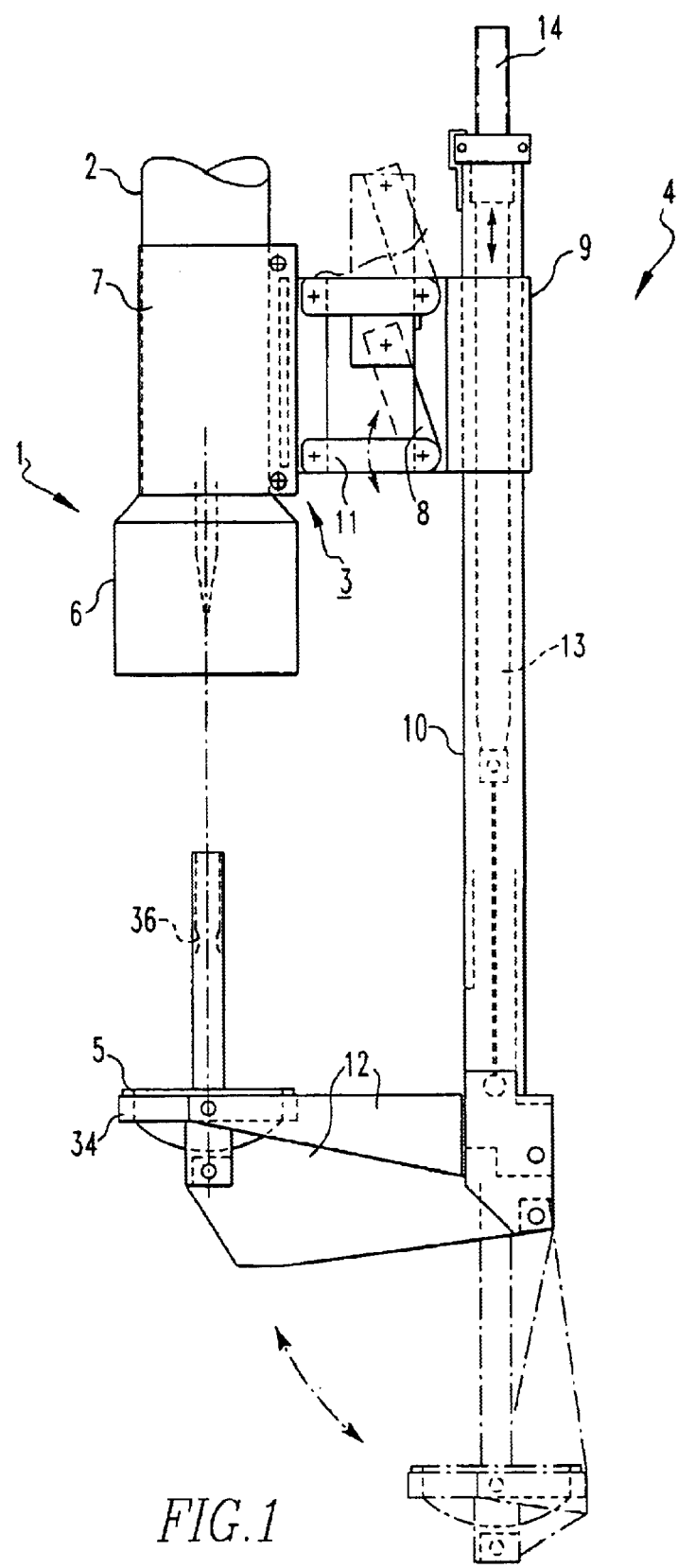
FIG. 1 is a side view of a guide structure connected to the shaft of a clamp suturing instrument.

FIG. 1 shows a clamp suturing instrument 1 with an operating shaft 2 on which a guide structure 4 for a counter-pressure plate 5 is supported by a coupling structure 3. The counter-pressure plate 5 includes a coupling thorn 35. The guide structure 4 is connected to the device shaft 2 immediately above a clamp magazine 6 by the coupling structure 3. The coupling structure 3 consists of a support part 7 for connection of the coupling structure 3 to the device shaft 2 and a coupling plate 8 for the connection of the coupling structure 3 to the guide member 9 of a guide tube 10. The support part 7 and the coupling plate 8 are pivotally interconnected by way of two lever pairs in the form of a parallelogram lever arrangement 11. By the guide member 9, which is connected to the coupling structure 3, the guide tube 10 is axially movably supported. At its lower end the guide tube 10 carries a lever pair 12, which is connected to a support member 34 of the counter pressure plate 5. The lever pair 12 can be operated by an operating linkage 13, which is disposed within the guide tube 10 and which is provided with an operating structure 14. By way of the linkage 13, the support member 34 for the counter pressure plate 5 can be moved together with the counter pressure plate 5 from its operating position as shown in FIG. 1 to a position in co-axial alignment with the guide tube 10 as it is shown in FIG. 1 by dashed lines.

For the procedure of inserting the instrument into the belly of a patient the guide member 9 is separated from the coupling plate 8 as shown in FIG. 2 and the coupling plate 8 is pivoted directly onto the device shaft 2 by means of an operating linkage 15, which is connected directly to the coupling plate 8 by pivoting the parallelogram lever pairs 11. The support member 34 supporting the counter pressure plate 5 is pivoted from the operating position, in which it extends co-axially with the device shaft 2 or, respectively, the clamp magazine 6, into an insert position, in which it extends co-axially with the guide tube 10 by way of the lever pair 12, which is operated by the operating linkage 13 disposed in the guide tube 10. After the pivot procedure, the guide member 9 and the support member 34 can be inserted through the trocar into the belly of the patient as the circumference of the structure has been substantially reduced. Subsequently, the device shaft 2 together with the clamp magazine 6 connected to the shaft 2 and the coupling structure 3 which is also connected to the device shaft 2 is inserted through the trocar into the belly. During the insertion procedure, the coupling plate 8 is held closely to the device shaft 2 by the operating linkage 15 so as to reduce the cross-section of the arrangement in this area of the device shaft 2.

Figure 3:
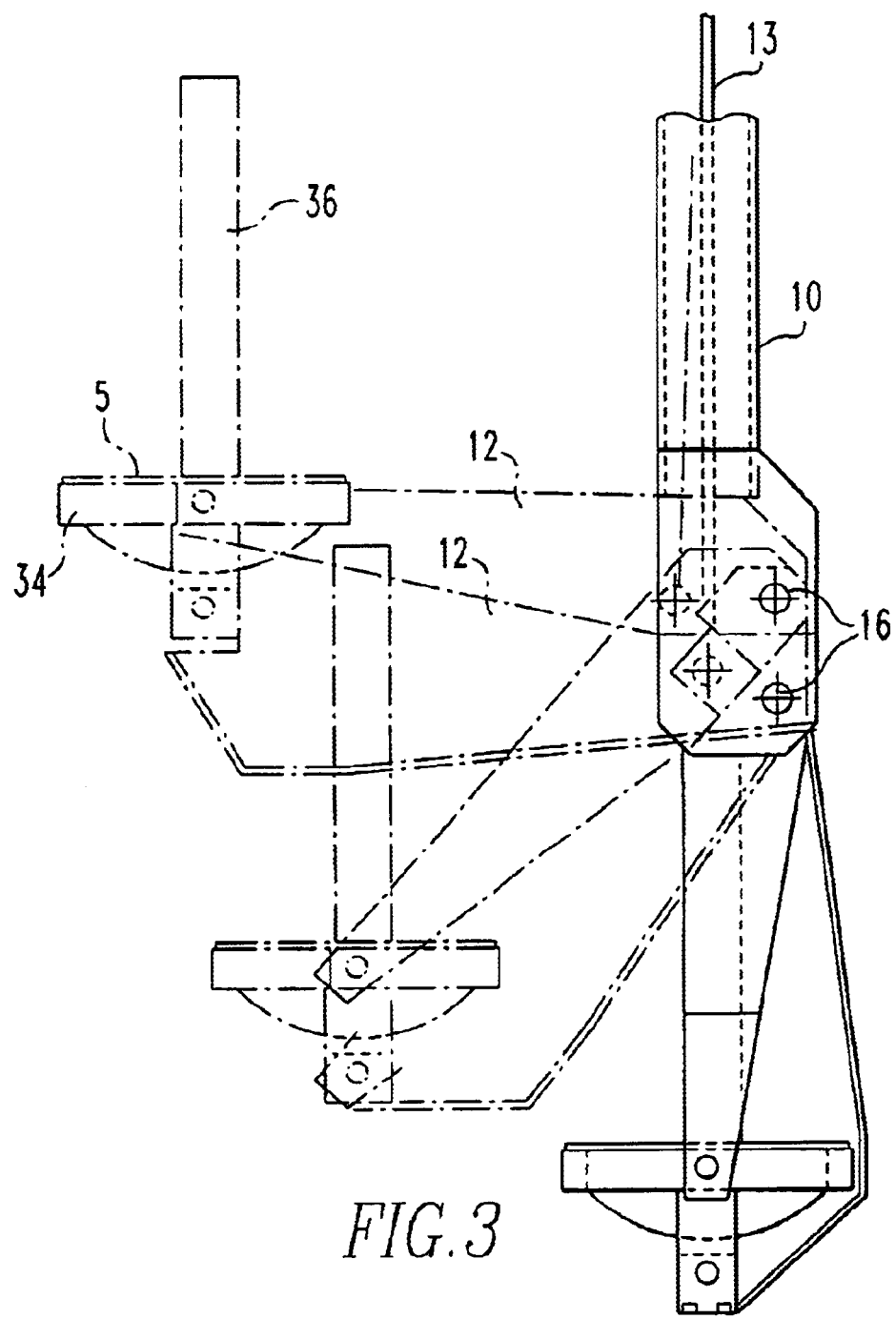
FIG. 3 is a side view of the support structure of the counter pressure plate and the lever pair which is assigned to the pressure plate and disposed at the end of the guide tube.

Within the belly, the coupling plate 8 and the guide member 9 are again joined for performing the operation. There, the counter pressure plate 5 is again pivoted out of its insert position co-axial with the guide tube 10 into the operating position in which it is co-axial with the device shaft 2, or respectively, the clamp magazine 6 by the operating linkage 13, which is disposed within the guide tube 13 and which engages the lever pair 12. The transfer procedure of the support member 34 from an insert position, in which it is co-axial with the guide tube 10, to a position, in which it extends co-axially with the device shaft 2 and parallel to the guide tube 10, is illustrated in FIG. 3. It is furthermore apparent from FIG. 3 that pivot joints 16 of the lever pair 13 at the guide tube 10 are arranged on top of one another in the axial direction of the guide tube 10.

Figure 4:
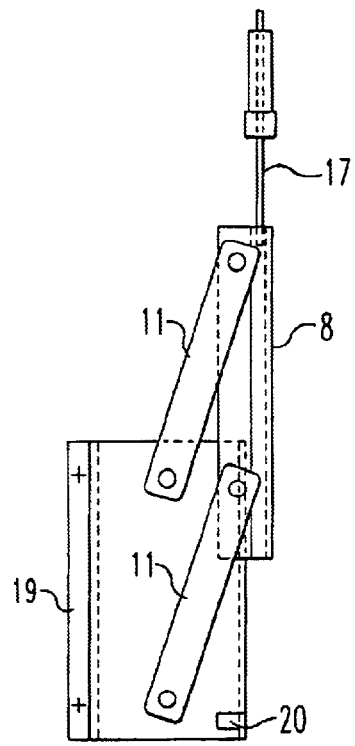
FIG. 4 is an enlarged side view of the coupling device with the operating structure for the pivot mechanism.

FIG. 4 is an enlarged representation of the coupling structure 3. The support part 7 of the coupling structure 3 is shown as a clamping sleeve 19, which is secured to the device shaft 2 by means of clamping screws or similar fastening means, which are not shown. The pivot movement of the coupling plate 8 is achieved in this embodiment by means of an operating cable 17 (Bowden control cable) connected to the coupling plate 8.

Figure 5:
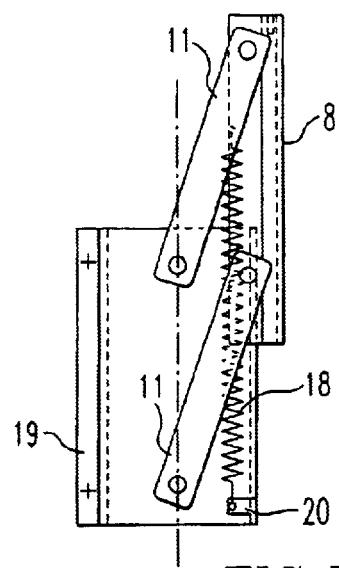
FIG. 5 is a side view of the coupling device with return springs.
Figure 6:
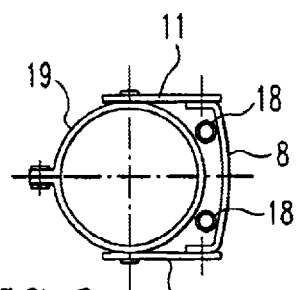
FIG. 6 is a top view of the coupling device with return springs.

If the pivoting of the coupling plate 8 out of its operating position is achieved by an operating cable 17 connected to the coupling plate 8, a return means must be provided by which the coupling plate 8, after insertion into the belly, can be pivoted back into its operating position. As shown in FIGS. 5 and 6, return movement of the coupling plate 8 is achieved by two parallel pull springs 18, which are connected to two parallelogram levers 11 arranged at opposite sides of the clamping sleeve 19 and engaging the clamping sleeve 19 in grooves 20.

As shown in FIGS. 7 and 8, the guide member 9 is held in engagement with the coupling plate 8 by an engagement spring or engagement tongue 21. The engagement spring or tongue 21 has an engagement cam 23, which is received in a corresponding engagement recess 22 of the coupling plate 8, see FIG. 9. The forces resulting from the engagement of the engagement spring or tongue are accommodated by a support member 24, which is arranged at the front side of the guide member 9 opposite the clamp magazine 6. The support member 24 extends beyond the contour of the guide member 9 and is angled downwardly so as to extend into a corresponding opening 25 in the coupling plate 8. The guide member 9 is accurately positioned relative to the coupling plate 8 by way of a centering pin 37 projecting from the guide member 9 and received in a complementary centering bore 38 formed in the coupling plate 8. As further apparent from FIG. 7, the guide tube 10 is axially secured within the guide member 9 by a spring-loaded engagement ball 27 disposed in a radial bore 26.

The opening 28 of the guide member 9 shown in FIG. 7 is provided for increasing the gripping capacity.

An alternative embodiment of the attachment structure for the mounting of a guide member 9 is represented in FIGS. 10 and 11. In the embodiment, guide panels 29 are provided at opposite surfaces of the guide member 9. They extend beyond the outer contour of the guide member 9 with their ends being angled toward each other. The guide panels 29 cooperate with complementarily shaped guide surfaces 30 of the coupling plate 8 and facilitate the assembly, that is, the coupling of the guide member 9 to the coupling plate 8 within the belly. The engagement spring 31 in this embodiment has an about U-shaped cross-section and includes essentially parallel legs 32 with V-like angled end portions 33. The engagement spring 31 is arranged on the guide structure 9 with respect to the guide panels 29 in such a way that the activation directions of the guide panels 29 and the parallel spring legs 32 extend at an angle of 90° relative to each other.

Figure 13:
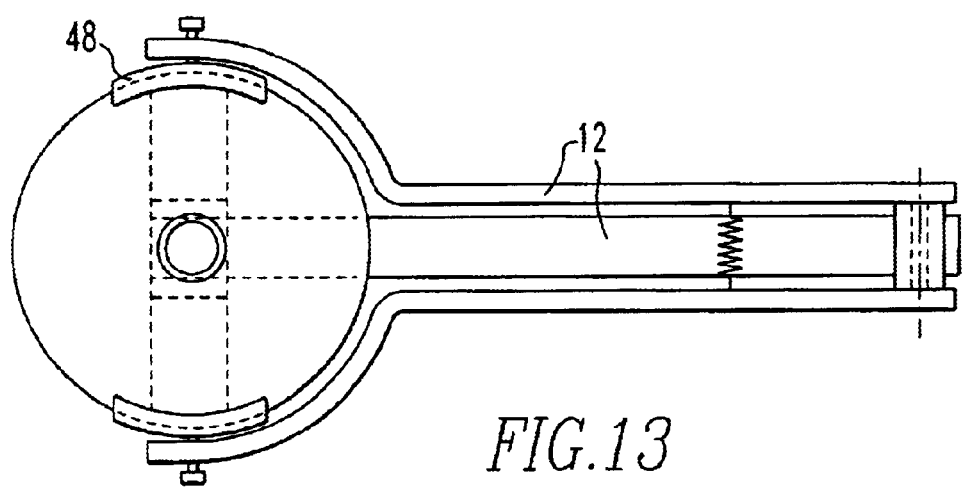
FIG. 13 is a top view of a support structure for a counter pressure plate.

FIG. 13 shows a preferred clamping device for fixing the counter pressure plate to the lever pair associated with this pressure plate. The clamping device comprises two clamping jaws 48 which engage the counter pressure plate radially and are arranged at the upper lever of the lever pair 12.

Figure 14:
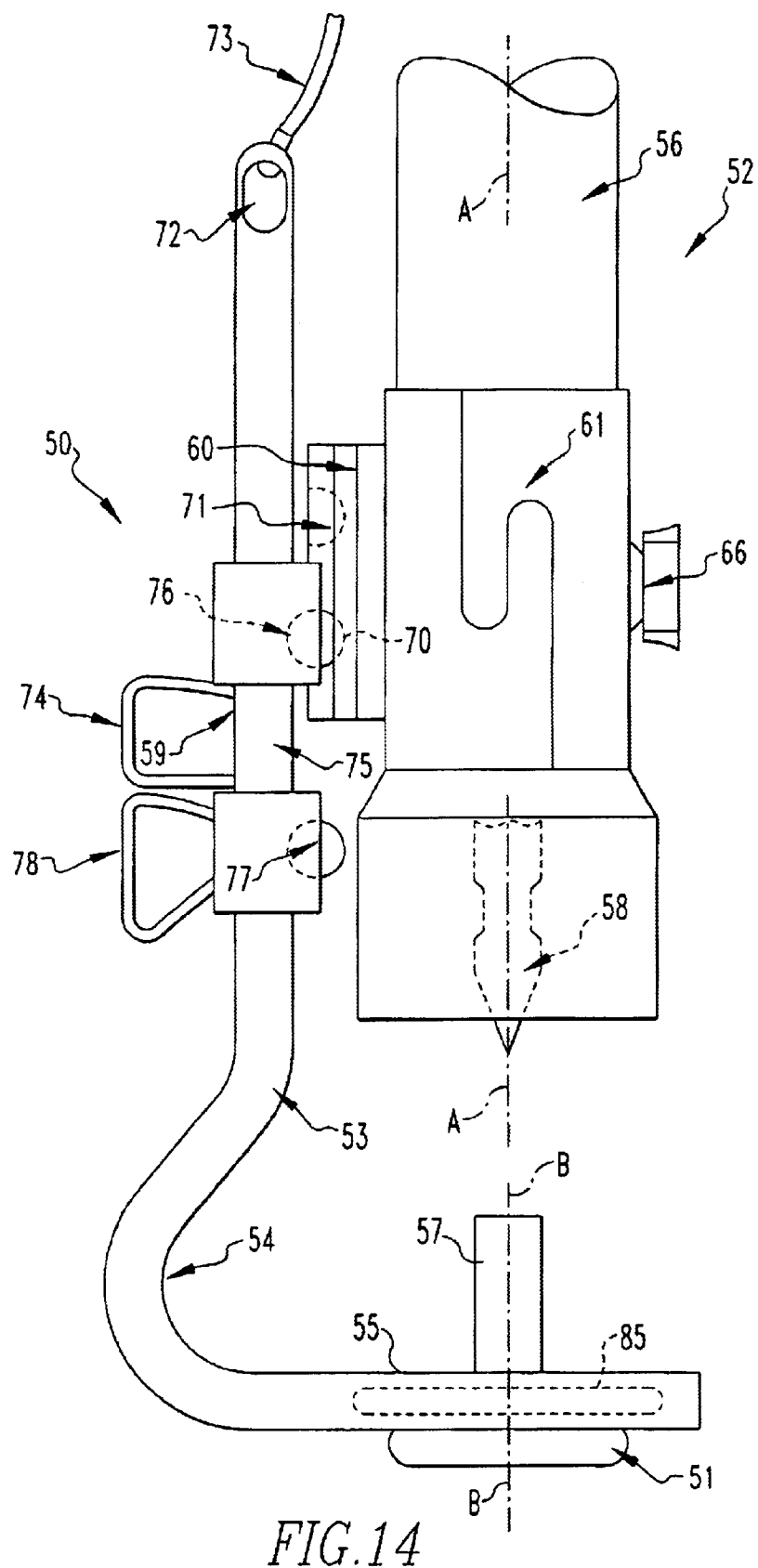
FIG. 14 is a schematic representation of a second embodiment of the arrangement according to the invention mounted to the distal end of a circular stapler or, respectively, a clamp suturing instrument.
Figure 15:
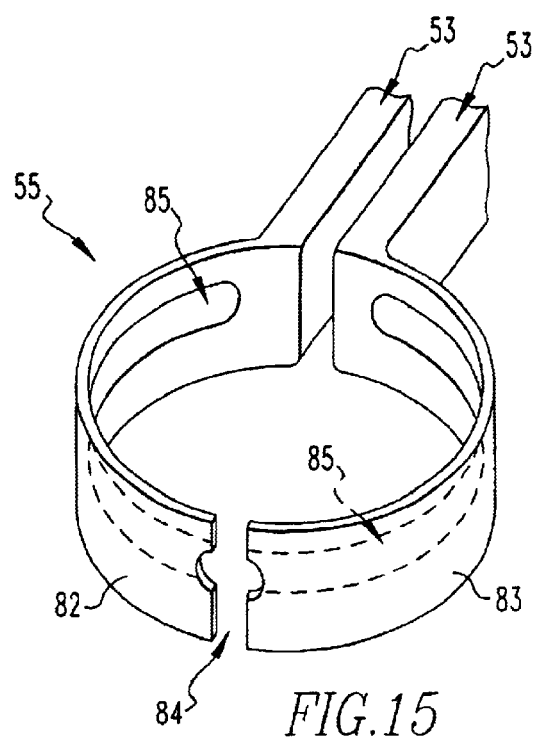
FIG. 15 is a schematic representation of the support section of the support structure without counter pressure plate.

FIGS. 14 and 15 show another embodiment of an arrangement 50 for properly supporting a counter pressure plate 51 for a shaft-like surgical clamp suturing instrument 52, wherein only the lower end of the clamp suturing instrument 52 is schematically shown. The arrangement 50 is formed, clasp-like, as a single part with two strand profile sections 53 and includes a sidewardly offset section 54 which extends to support section 55 for releasably supporting the counter pressure plate 51. The support section 55 extends normal to the shaft section 56. The center, that is the center axis B—B,
of the counter pressure plate 51, which extends through the receiver shaft 57 extending from the counter pressure plate 51, is in axial alignment with the shaft axis A—A.

Of the clamp suturing instrument, only the lower section is shown schematically. A coupling thorn 58, which is received in the lower section is extendable therefrom for connection to the receiver shaft 57 of the counter pressure plate 51. The coupling thorn 58 is shown in dashed lines.

Figure 17:
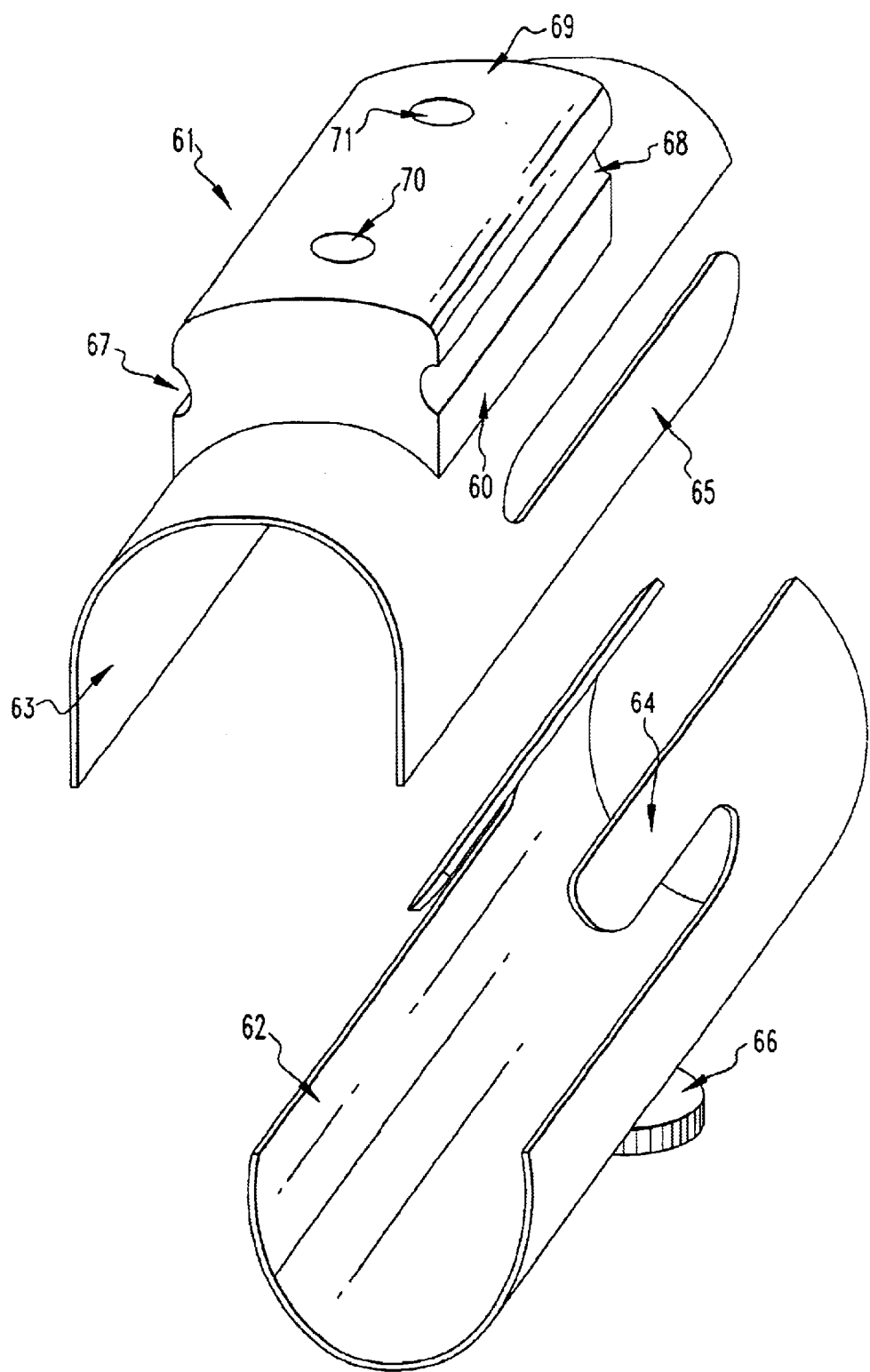
FIG. 17 is an exploded view of the support and guide structure.

The support structure 50 includes a sled-like connecting section 59, which is mountable to a complimentary profile section of a support and guide structure 61 mounted to the distal shaft section 56 of the clamp suturing instrument 52. It is slideable between at least two operating positions and it can be removed from the support structure 61. As apparent from FIG. 17, the support and guide structure 61 consists of a two-part mounting sleeve with a shaft mounting part 62 and a profile section 63 for the connecting section 59. The two mounting sleeve parts 62 and 63 have portions 64 and 65, respectively, by which the parts can be bayonet-like engaged, and when engaged can be easily disengaged. They provide for a secure connection between the two parts. Additionally, a lock screw 66 may be provided for the safe engagement between the two parts.

The profile section 60 is mounted onto the profile section 63. It includes at its side two slide guide grooves 67 and 68 and a support surface 69 with engagement openings 70 and 71 arranged in a line extending parallel to the axis of symmetry A—A of the shaft 56 of the clamp suturing instrument. The support surface is transversely curved in the shown embodiment and the slide guide grooves 67 and 68 have a radius of curvature which is so adapted to that of the rod profiles of the clasp-like support member that they are engaged at least with some parts of their surfaces.

The support structure 10 as shown in FIG. 14 extends beyond the connecting section 59 upwardly and at its upper end, it includes an opening 72 for the attachment of a pull member 73 such as a rope. As shown in FIG. 18, the connecting section 59 is provided with two bow-like handling members 74, which are mounted to two spring-supported profile sections 75 of the clasp-like support structure 50. Upon compression of the two bow-like handling members 74, the bolt sections 75 are slightly spread apart so as to facilitate the mounting of the support structure 50 onto the slide guide grooves 67, 68 and the surface 69 of the profile section 60. As further apparent from FIG. 19, the sled-like connecting section 59 includes two compression spring supported engagement balls 76 and 77 at the side opposite the handling members 74. The engagement balls 76 and respectively, 77 are provided for engagement with the engagement openings 70 and 71, respectively, in order to secure at least two rest positions for the support member 50 with respect to the clamp suturing instrument 52.

Another bow-like handling member 78, which, for simplification, is not shown in FIG. 18, is shown schematically in FIGS. 14 and 19. This bow-like handling member 78 is mounted to the lower area of the connecting section 59 and is used to move the whole support structure 50 beyond the carriage-like connecting section 59 at the profiled guide section 60 and for the release of the support member 50.

FIG. 19 shows the rear side of the support structure 30 as shown in FIG. 14, wherein the bow-like handling member 78 is mounted to a horizontal section 79, which extends parallel to the horizontal guide sections 80 and 81 of the sled-like connecting section 59.

Figure 16:
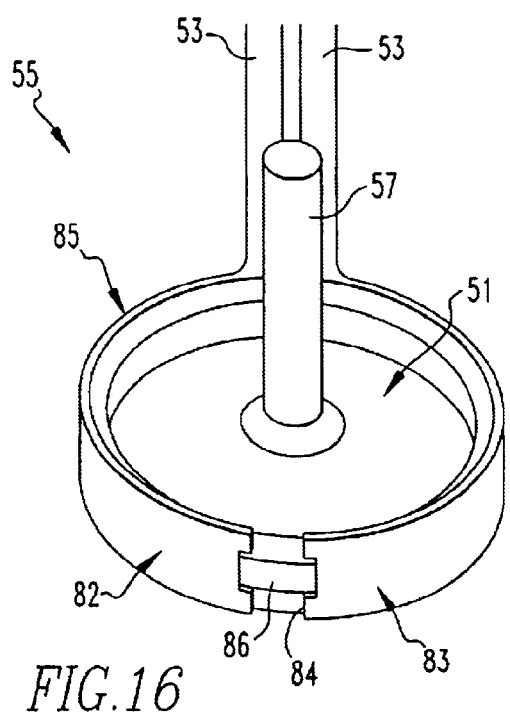
FIG. 16 shows the support section of FIG. 15 with the counter pressure plate engaged therein.

As can be seen in connection with FIGS. 15 and 16, the support section 55 is formed by two annular segments 82 and 83, which are attached to the lower end of the clasp-like mounting structure 50. Between the annular sections 82 and 83, there is a gap 84 which permits spreading of the support section 55. The support section 55 includes a groove-like recess 85 in which the outer circumference 86 of the counter pressure plate 51 is received as shown in FIG. 16. The counter pressure plate 51 can be held by the annular sections 82 and 83 without spring means that compress the annular sections 82. However, springs may be provided for compressing the annular sections 82.

For the handling of the arrangement 50, first the two sleeve sections 62 and 63 are attached to the shaft 56 of the circular stapler or, respectively, the clamp suturing instrument 52 and joined by the bayonet type portions 64, 65. Subsequently, a safe connection is established by way of the set screw 66. Then, the support structure 50 is attached by way of a slide-like connecting section 59 to the profile section 60 of the profile part 63 by pressing the bow-shaped handling members 74 toward each other whereby the associated bolt-like portions 75 are spread apart and, after placement onto the profile section 60, are received in the guide grooves 67 and 68. In this process, the support structure 50 is first brought to the engagement position as shown in FIG. 14, wherein the support section 55 with the counter pressure plate 51 has the greatest possibly distance from the distal end of the shaft-like clamp suturing instrument 52. In this way, it is possible to move the counter-pressure plate 51 with the shaft 57 extending therefrom behind the rear stomach wall. The counter pressure plate is inserted into the support section 55 still outside the body and is safely held received in a form-fitting manner in the groove 85 of the support section.

Then, by way of a small incision in the upper quadrant of the abdomen, the support member connected to the circular stapler or clamp-suturing instrument is inserted into the belly. Earlier, a space has been determined at the small curvature of the stomach into which the counter pressure plate 51 is introduced. With the particular shape of the support section 55 with the sidewardly offset section 54, the front and the rear wall of the stomach are engaged at the small curvature in a clamp-like fashion. The required dimensions for the stomach pouch are given by the shape of the support member. This means that the offset section 54 of the support structure 50 should be adjusted, as necessary, that is, the offset section may extend more or less from the longitudinal axis A—A of the clamp suturing instrument.

When the counter pressure plate 51 is located by the surgeon behind the stomach in a "blind" way, the support structure 50 is moved to a second engagement position on the support and guide structure by pulling on the pull member 73. In this position, the thorn 58 can be moved out of the head of the circular stapler or clamp suturing instrument 52 whereby it penetrates the stomach walls and, guided by the support structure 50, accurately enters the shaft 57 of the pressure plate 5. Within the shaft 57, the thorn is safely retained by way of a spring mechanism, which is not shown.

By actuation of the bow-like handling members 74 and 78, the support member can then be released from the support and guide structure 60 and deposited nearby. Subsequently, the counter pressure plate 51 is finally pulled toward the head of the circular stapler whereupon a circular clamp seam is established and, at the same time, a circle is cut into the front and rear walls of the stomach.

Then the circular stapler or clamp suturing instrument 52 is removed from the abdomen together with the cut-out stomach portions and finally, also the support structure 50 is pulled out of the abdomen by means of the pull member 73.

What is claimed is:

1. An arrangement for supporting a counter pressure plate including a receiver shaft having a center axis coaxial with the counter pressure plate for establishing a circular seam, said arrangement comprising a shaft-like clamp suturing instrument having a shaft section with a distal end, a support and guide structure disposed at the distal end of said shaft section and a one-piece support structure axially movably supported on said support and guide structure so as to be releasable therefrom, said support structure including an offset section and a support portion extending normal to said shaft section and a back-pressure plate supported by said support portion such that the center axis of said back-pressure plate is in axial alignment with the axis of said shaft section.

2. Arrangement as defined in claim 1, wherein said one-piece support structure is clasp-shaped and said support portion is provided at a widened end thereof.

3. An arrangement according to claim 1, wherein said support portion of said one-piece support structure comprises two semi-circular halves including profiled groove-like recesses for receiving at least portions of the outer circumference of said counter pressure plate in a form-fitting manner.

4. An arrangement according to claim 1, wherein said semicircular halves are movable apart for releasing said counter pressure plate.

5. An arrangement according to claim 4, wherein said semicircular halves have a diameter which is slightly smaller than that of said counter pressure plate for resiliently engaging said counter pressure plate.

6. An arrangement according to claim 1, wherein said support structure includes a sled-like connecting section for joining to a complementary profile section of the support and guide structure disposed at a distal shaft section of said clamp suturing instrument, said support structure being slidable longitudinally along said support and guide structure between at least two engagement positions and being removable from said support and guide structure.

7. An arrangement according to claim 6, wherein said sled-like connecting section of said support structure comprises a clamping section with two parallel legs extending between spaced transverse guide sections.

8. An arrangement according to claim 6, wherein said sled-like connecting section includes at least two engagement structures providing secure locking positions for the support and guide structure.

9. An arrangement according to claim 6, wherein said support and guide structure includes a two-part profiled sleeve portion including a shaft mounting section and a profiled mounting section.

10. An arrangement according to claim 9, wherein said two profiled sleeve portions include cut outs and projections, the cutouts of each portion being adapted to receive the projections of the other for engagement of the two.

11. An arrangement according to claim 6, wherein for the axial movement and the release of the connecting section bow-like handling members are connected to said profile portions.

12. An arrangement according to claim 1, wherein said support structure includes, at its end opposite the support section, means for the connection of a pull member.

* * * * *